US012303150B2

(12) United States Patent
Wong et al.

(10) Patent No.: US 12,303,150 B2
(45) Date of Patent: May 20, 2025

(54) CUT GUIDE, SYSTEMS, AND METHODS

(71) Applicant: Wright Medical Technology, Inc., Memphis, TN (US)

(72) Inventors: Kian-Ming (Kevin) Wong, Lakeland, TN (US); Johnny McGee, Halls, TN (US)

(73) Assignee: WRIGHT MEDICAL TECHNOLOGY, INC., Memphis, TN (US)

(*) Notice: Subject to any disclaimer, the term of this patent is extended or adjusted under 35 U.S.C. 154(b) by 629 days.

(21) Appl. No.: 17/648,233

(22) Filed: Jan. 18, 2022

(65) Prior Publication Data

US 2022/0265288 A1 Aug. 25, 2022

Related U.S. Application Data

(60) Provisional application No. 63/152,941, filed on Feb. 24, 2021.

(51) Int. Cl.
*A61B 17/15* (2006.01)
*A61B 17/17* (2006.01)
*A61B 17/56* (2006.01)

(52) U.S. Cl.
CPC .......... *A61B 17/1775* (2016.11); *A61B 17/15* (2013.01); *A61B 2017/565* (2013.01)

(58) Field of Classification Search
CPC ... A61B 17/15; A61B 17/151; A61B 17/1775; A16B 2017/565
See application file for complete search history.

(56) References Cited

U.S. PATENT DOCUMENTS 5,597,379 A * 1/1997 Haines ............... A61B 17/1764
606/88
5,843,085 A * 12/1998 Graser ............... A61B 17/151
606/87
6,945,976 B2 * 9/2005 Ball ..................... A61B 17/1739
606/86 R (Continued)

FOREIGN PATENT DOCUMENTS

CN 107007319 A 8/2017
WO 2015105880 A1 7/2015
WO 2020231490 A1 11/2020

OTHER PUBLICATIONS

Partial European Search Report issued in connection with European Patent Application No. 22158462.6, Jul. 22, 2022, 12 pages.

(Continued)

*Primary Examiner* — Nicholas W Woodall
(74) *Attorney, Agent, or Firm* — DUANE MORRIS LLP

(57) ABSTRACT

A cut guide includes a body having a first face and an opposed second face. The first face of the body defines first and second apertures, a first fixation hole, and an attachment hole. The first and second apertures are configured to guide a surgical tool, and the first fixation hole extends through the cut guide from the first face to the second face and is configured to receive a wire to position the cut guide against a bone. The attachment hole is configured to attach the cut guide to another component. A system including the cut guide and methods of using the system also are disclosed.

25 Claims, 11 Drawing Sheets

(56) References Cited

U.S. PATENT DOCUMENTS

| | | | | |
|---|---|---|---|---|
| 7,887,542 | B2* | 2/2011 | Metzger | A61B 17/155 |
| | | | | 606/87 |
| 8,475,462 | B2* | 7/2013 | Thomas | A61B 17/15 |
| | | | | 606/87 |
| 10,849,663 | B2* | 12/2020 | Dayton | A61B 17/15 |
| 11,259,817 | B2* | 3/2022 | Fallin | A61B 17/151 |
| 11,839,383 | B2* | 12/2023 | Boffeli | A61B 17/66 |
| 2007/0265634 | A1* | 11/2007 | Weinstein | A61B 17/15 |
| | | | | 606/87 |
| 2007/0270850 | A1* | 11/2007 | Geissler | A61B 17/80 |
| | | | | 606/326 |
| 2016/0213384 | A1 | 7/2016 | Fallin et al. | |
| 2018/0250019 | A1 | 9/2018 | Nguyen et al. | |

OTHER PUBLICATIONS

Extended European Search Report issued in connection with European Patent Application No. 22158462.6, Oct. 25, 2022, 11 pages.

* cited by examiner

CUT GUIDE, SYSTEMS, AND METHODS

TECHNICAL FIELD

This application claims benefit to U.S. Provisional Application No. 63/152,941, filed Feb. 24, 2021, the disclosure of which is incorporated herein by reference in its entirety.

TECHNICAL FIELD

The disclosed system and method relate to the field of correcting anatomical structures. More particularly, the disclosed systems and methods relate to correcting defects in anatomical structures in the lower extremities of a patient.

BACKGROUND

Hallux valgus deformities (also known as bunions) occur when a metatarsal goes into a varus state (i.e., is pointed inwardly). In addition to being pointed inward, the metatarsal also may be rotated about its longitudinal axis such that the bottom of the bone is facing outwardly, which may result in the sesamoid being pointed outwardly when it should be located underneath the metatarsal. Correction of a bunion typically requires surgery, such as a performing a Chevron osteotomy. Such procedures may also include a compression operation and/or insertion of one or more screws into the patient's foot to assist with the correction. Disclosed embodiments include systems and methods for addressing these and/or other anatomical issues and providing benefits over existing solutions.

SUMMARY

In some embodiments, a cut guide includes a body having a first face and an opposed second face. The first face of the body defines first and second apertures, a first fixation hole, and an attachment hole. The first and second apertures are configured to guide a surgical tool, and the first fixation hole extends through the cut guide from the first face to the second face and is configured to receive a wire to position the cut guide against a bone. The attachment hole is configured to attach the cut guide to another component.

In some embodiments, a system includes a cut guide, a compression device, and a a first connector. The cut guide has a body including a first face and an opposed second face. The first face of the body defines first and second apertures, a first fixation hole, and an attachment hole. The first and second apertures are configured to guide a surgical tool. The first fixation hole extends through the cut guide from the first face to the second face and is configured to receive a wire to position the cut guide against a bone. The compression device has a base and a compression head, which is movable relative to the base. The first connector is sized and configured to couple to the compression device to the cut guide via the attachment hole.

In some embodiments, a method includes coupling a first wire to a first bone of an appendage of a patient; coupling a cutting guide to the first wire; inserting a second wire into a first fixation hole defined by the cutting guide and into the first bone; resecting the first bone using a surgical tool and the cutting guide; attaching a compression device to the cutting guide; and compressing the appendage of the patient using the compression device.

BRIEF DESCRIPTION OF THE DRAWINGS

The features of the present disclosure will be described in more detail in conjunction with the following drawing figures. The structures in the drawing figures are illustrated schematically and are not intended to show actual dimensions.

DETAILED DESCRIPTION

Figure 1:
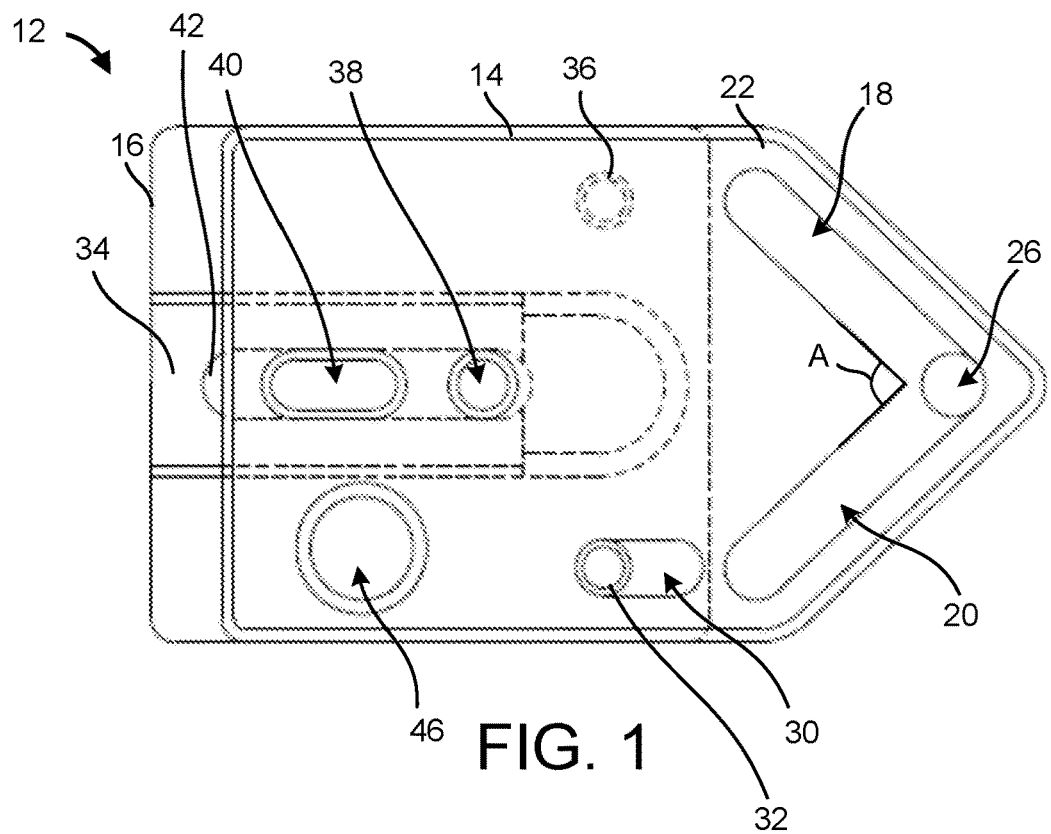
FIG. 1 is a front view of an exemplary cut guide in an extended position, according to disclosed embodiments.

This description of the exemplary embodiments is intended to be read in connection with the accompanying drawings, which are to be considered part of the entire written description.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

Figure 2:
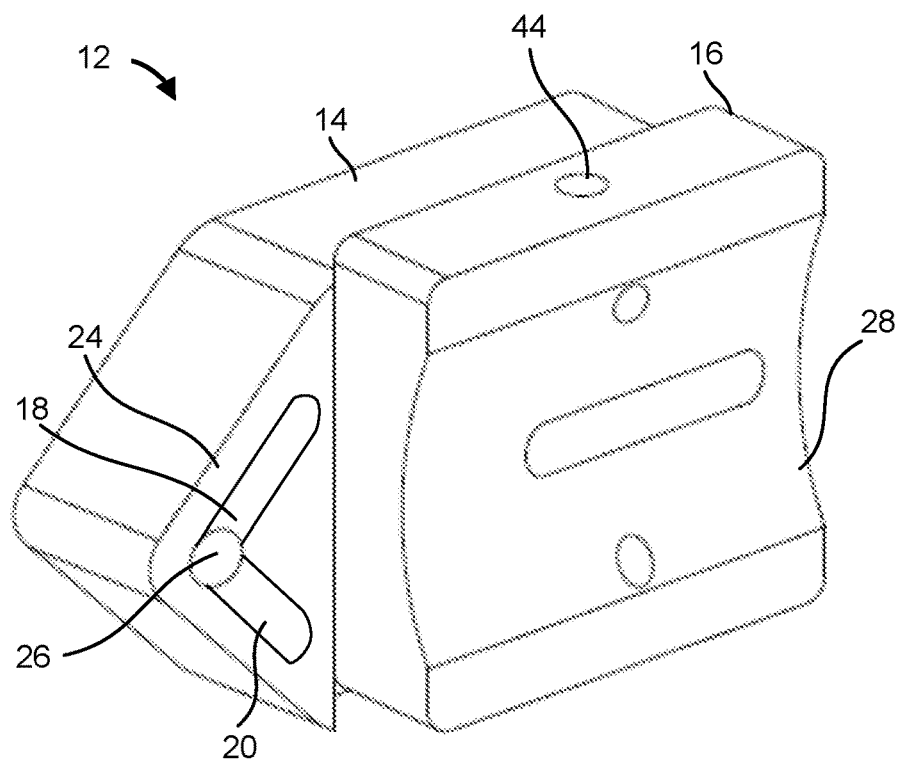
FIG. 2 is a rear isometric view of the cut guide of FIG. 1, according to disclosed embodiments.
Figure 3:
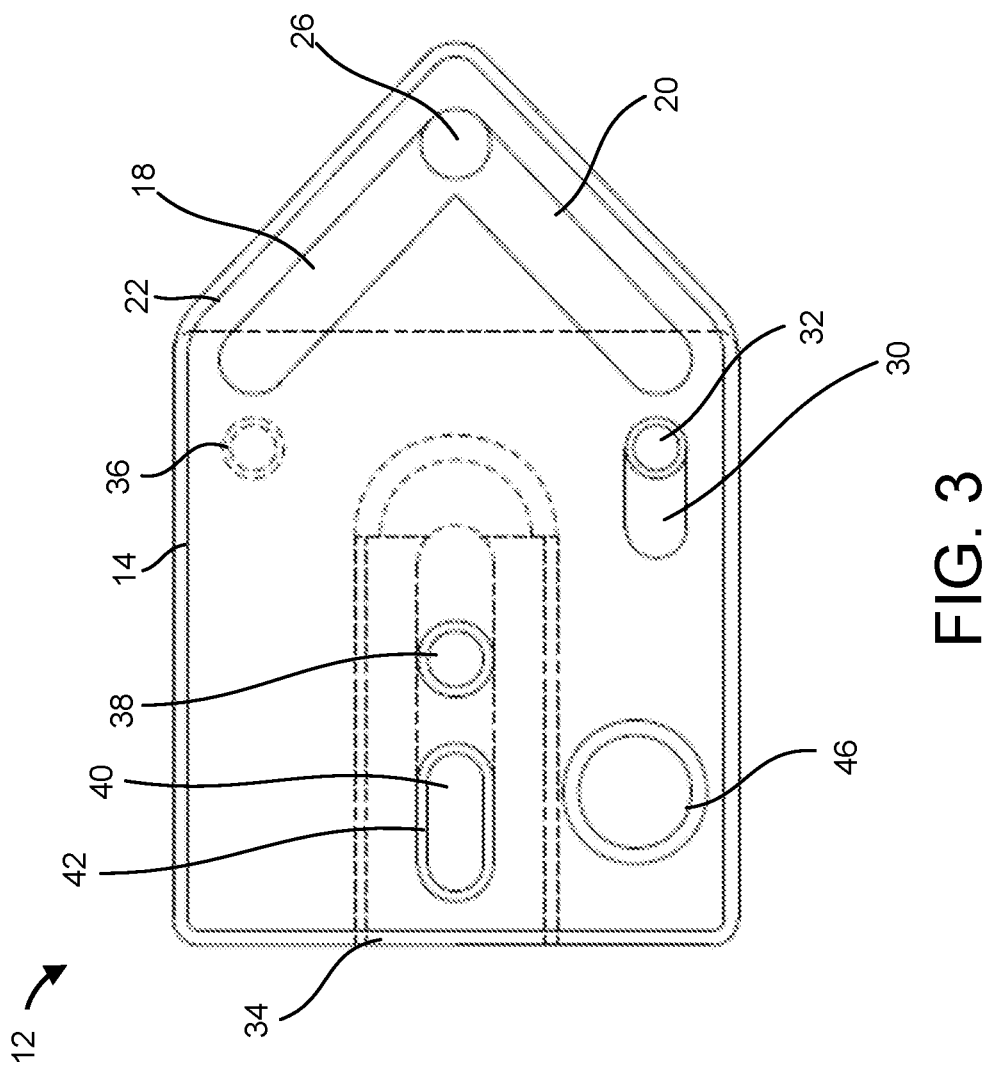
FIG. 3 is a front view of the cut guide of FIG. 1 in a collapsed position, according to disclosed embodiments.

This disclosure describes cutting guides and targeting guides and methods of their use. The cutting guides and targeting guides described herein are particularly well suited for use in procedures to correct pronounced hallux valgus angles of the first toe. However, they may be used in any appropriate procedure FIGS. 1-8 show a first embodiment of a guiding system 10 that includes a cut guide 12. FIG. 1 shows a front view of the cut guide 12. The cut guide 12 can include a first part 14 and a second part 16 that fits together with the first part 14. The first part 14 and the second part 16 can be slidably movable with respect to each other between at least an extended position (FIG. 1) and a collapsed position (FIG. 3). The first part 14 and the second part 16 can also include one or more intermediate positions in some embodiments. While embodiments are described as two-parts, it should be understood that the disclosed cut guide is not limited to this configuration. In some embodiments, a one-piece cut-guide can be used. In other embodiments, a cut guide can include more than two parts without departing from the scope of the present disclosure.

In some embodiments, the first part 14 of the cut guide 12 can include a first aperture 18 and a second aperture 20 extending between a first face 22 and a second face 24 of the cut guide 12. The first aperture 18 and the second aperture 20 can be elongated slots as shown in the illustrated embodiments or can include other shapes depending on a medical procedure. The first aperture 18 and the second aperture 20 can include any suitable depth in the first face 22, including being open holes through the second face 24. The first aperture 18 and the second aperture 20 are configured to guide a cutting instrument (e.g., a surgical saw) in cutting a bone. In one embodiment, the first and second apertures 18, 20 are oriented at an angle A with respect to one another such that the cutting instrument can form a chevron-shaped cut in a bone, as will be described herein. For example, in some embodiments, the first and second apertures 18, 20 are oriented at an angle of about 45 degrees with respect to one another. However, it should be understood that the angles of the first and second apertures 18, 20 are not limited as such and can include any angles in a range of 0.1 degrees to 360 degrees. In some embodiments, the first and second apertures 18, 20 meet at an intersection. The first and second apertures 18, 20 can be the same length or can be different lengths and positioned at different angles relative to one another. The first and second apertures 18, 20 can be connected to each other as a single aperture such as in embodiments in which one large opening is formed between the first face 22 and the second face 24, including the areas of the first and second apertures 18, 20. For example, a single triangle-shaped opening may be formed with the first and second apertures 18, 20 being portions along two sides of the triangle-shaped opening. The cut guide 12 can be provided in both a left and right configuration for use on the left and right foot, respectively. In some embodiments, the cut guide 12 is configured to be universal (i.e., it may be used for both a "left" and a "right" extremity or body part).

In some embodiments, the cut guide 12 further includes a first hole 26 extending between first face 22 and second face 24. In some embodiments, the first hole 26 can be configured to guide a surgical tool, such as a tool for cutting the patient's bone in a deburring operation. In some embodiments, the first hole 26 can be additionally or alternatively configured to receive a k-wire, Steinmann pin, or other appropriate wire or pin (hereinafter, k-wires, Steinmann pins, and other wires or pins are collectively referred to as a "wire") inserted into a bone of a patient, as described herein. In some embodiments, the first hole 26 is positioned at the intersection of first and second apertures 18, 20.

The first part 14 of the cut guide 12 which includes the first and second apertures 18, 20 and thus be a cutting portion of the disclosed embodiments. The second part 16 can be a separate structure from the first part 14 and be configured to fit within a portion of the first part 14. The second part 16 can include a contacting surface 28 configured to contact a patient's foot. The contacting surface 28 can include any selected configuration, such as a curved surface, flat surface, can include grooves or a roughened surface, etc.)

In some embodiments, the first part 14 and the second part 16 can be configured to be slidably movable with respect to each other between an extended configuration shown in FIG. 1 and a collapsed configuration shown in FIG. 3. This sliding configuration of the cut guide 12 can be used to set a predetermined resection distance. A slot and pin configuration can be used to enable this slidable configuration. For example, the first part 14 can include a retaining slot 30 and the second part 16 can include a retaining pin 32 that fits within the retaining slot 30. The provision of the retaining slot 30 and the retaining pin 32 could be reversed between the first part 14 and the second part 16, in some embodiments. The retaining slot 30 can be any appropriate shape and the retaining pin 32 can be round, square, hexagon, etc. The retaining pin 32 can be knurled, splined, etc. In some embodiments, the first part 14 and the second part 16 can include a sliding mechanism 34, such as a t-slot, dovetail connection, etc., to guide the relative sliding movement of the first part 14 and the second part 16 between limits established by the guide slot 30 and guide pin 32. The first part 14 and the second part 16 can further include a locking mechanism 36, such as a ball detent using a spring and ball (or ball plungers, wave washer, etc.) that engages a spherical hole. The locking mechanism 36 can be configured to lock the first part 14 and the second part 16 with respect to each other to create a preset resection distance. One of ordinary skill in the art will understand that other types of locking mechanisms may be used (e.g., locking or set screws, interference fits, and/or detents of other configurations and/or shapes, to list only a few possibilities).

In some embodiments, the locking mechanism 36 locks the cut guide 12 in the collapsed configuration shown in FIG. 3. In some embodiments, the locking mechanism 36 can include a plurality of locking positions for selecting from a plurality of preset resection distances. In some embodiments, the collapse distance of the sliding part is equal to or greater than a material thickness of the cut guide 12. In some embodiments, the collapse distance of the sliding part is less than a material thickness of the cut guide 12.

The cut guide 12 can also include wire-features including a first fixation hole 38 in the first part 14, a second fixation slot 40 in the first part 14, and a fixation clearance slot 42 in the second part 16. The first fixation hole 38 and the second fixation hole 40 may be at least partially aligned with the fixation clearance slot 42 such that a wire can pass through both the first part 14 and the second part 16 (i.e., to reach a patient bone). In some embodiments, one or more of the first fixation hole 38 and the second fixation 40 have other geometries and/or configurations that provide clearance for pins. In some embodiments, for example, the geometry and/or configuration of the fixation hole 38 and slot 40 depends on the configuration of the cut guide 12 in an extended or collapsed configuration. For example, the second fixation hole 40 can be a slot to accommodate a plurality of positions for a wire to pass through the fixation hole 40 and the fixation clearance slot 42. In some embodiments, the first part 14 and/or second part 16 can additionally or alternatively include other fixation holes for receiving wires. For example, as shown in FIG. 2, the second part 16 can include a fixation hole 44 in a top portion of the second part 16. The fixation hole 44 can be provided in any shape or provided as multiple fixation holes. The fixation hole 44 can be formed at any angle through the second part 16 and have any size, depending on the fixation required or desired.

In some embodiments, the cut guide 12 can also include an attachment hole 46. The attachment hole 46 can be configured to attach the cut guide 12 to another component for use in the medical procedure, as will be described herein. The attachment hole 46 can be a threaded hole, a twist lock, bolt attachment, or any selected attachment mechanism.

Figure 4:
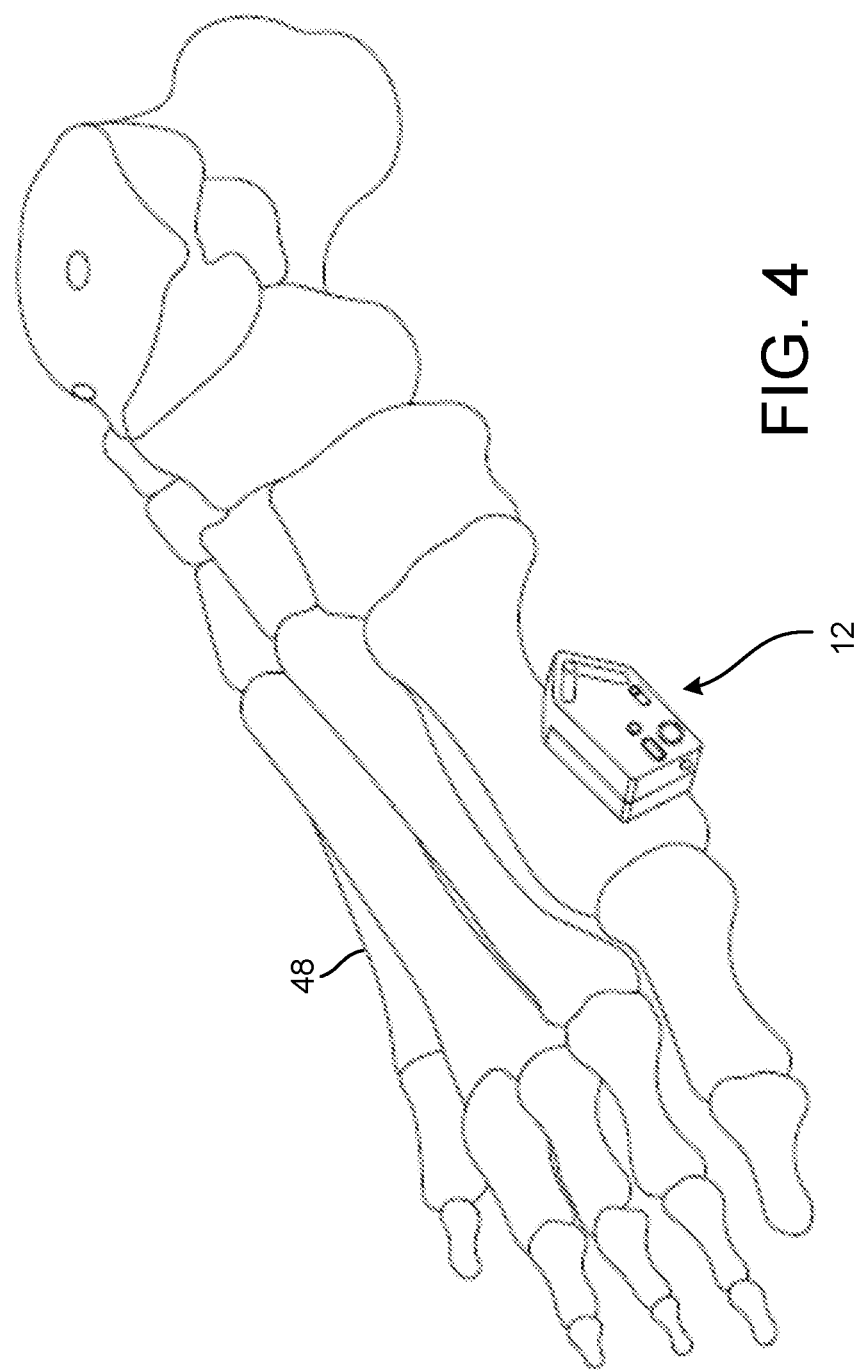
FIG. 4 is a isometric view of the cut guide of FIG. 1 positioned in relation to a skeletal foot, according to disclosed embodiments.

FIG. 4 illustrates an example of the cut guide 12 on a skeletal foot 48. The cut guide 12 can be attached to the foot 48 using wires inserted through one or more of the fixation holes of the cut guide 12. For example, a wire can be attached to a metatarsal head of the foot 48 and the cut guide 12 slid over the wire via the fixation hole 38 and clearance slot 42. The cut guide 12 can be additionally positioned and attached by additional wires, such as by a wire inserted through the second fixation hole 40 and the clearance slot 42. In some embodiments, the cut guide 12 is aligned with the metatarsal axis prior to inserting a second wire, and an additional fixation wire may be inserted through hole 44 once the cut guide has been aligned with the metatarsal axis. The cut guide 12 can then be used to guide cutting during a medical procedure, such as a resection performed with a saw inserted into the first and second apertures 18, 20 and/or first hole 26.

In exemplary embodiments, the cut guide 12 can be configured to attach to additional components of the guiding system 10 for additional steps of a medical procedure involving the cut guide 12, such as to perform compression or urge movement of one or more bones of the foot 48 while the cut guide 12 remains attached to the foot 48. In this way, the cut guide 12 can act as a base/support or point of attachment for the additional components.

Figure 5:
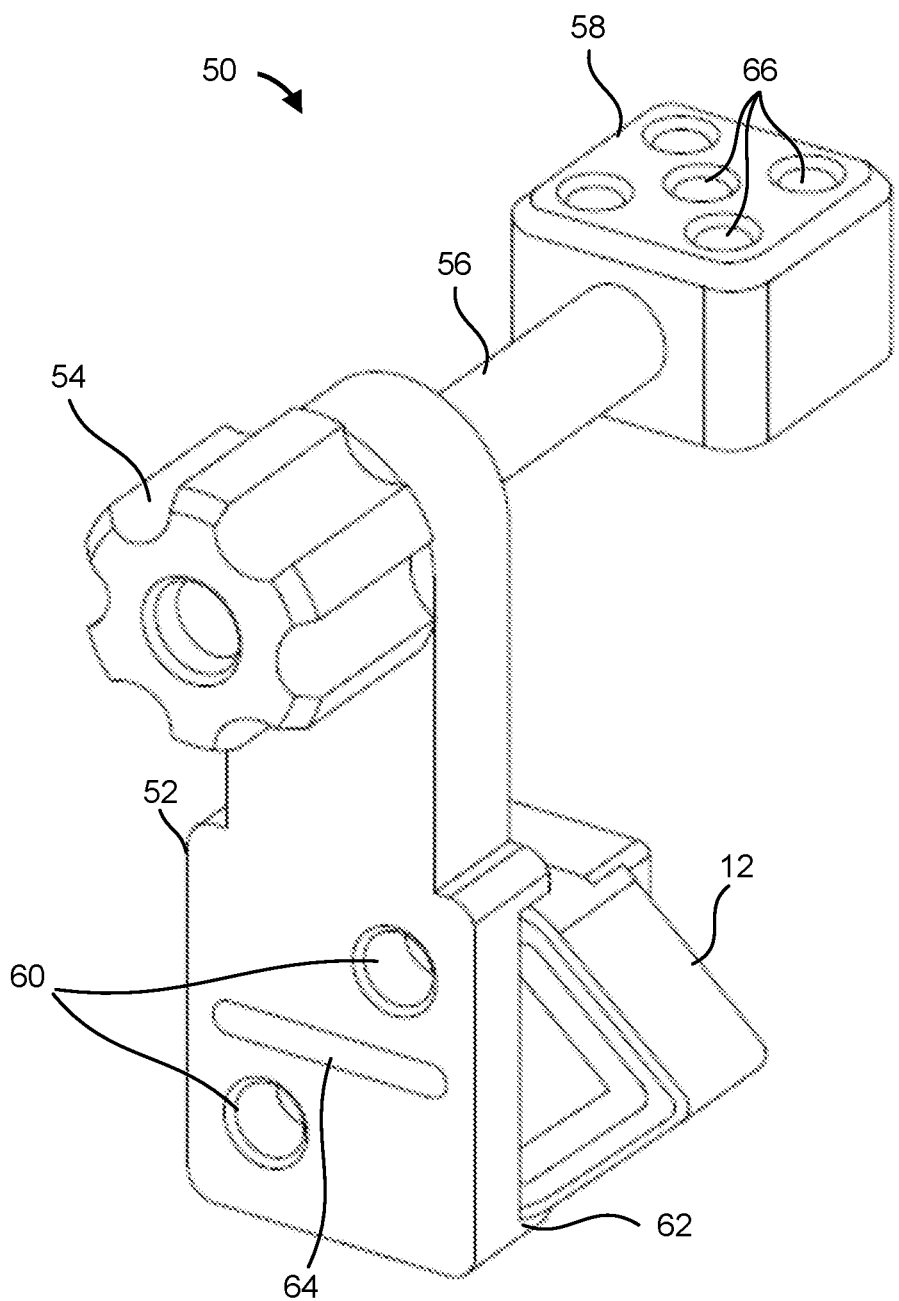
FIG. 5 is an isometric view of a compression device attached to the cut guide of FIG. 1, according to disclosed embodiments.

FIG. 5 illustrates an embodiment of a compression device 50 attached to the cut guide 12. The compression device 50 can include a base 52, a compression knob 54, a compression shaft 56, and a compression head 58. The base 52 can be configured to attach to the cut guide 12. For example, the base 12 can be configured to attach to the first part 14 of the cut guide 12 through the attachment hole 46. For instance, the base 12 can include one or more through-holes 60 for aligning with the attachment hole 46 to receive a fastener therethrough. In some embodiments, the base 12 can include a plurality of through-holes 60 for aligning with the attachment hole 46 depending on a desired orientation of the compression device 50 (e.g., depending on whether the device is being used on a left or right foot). The base 52 can also include one or more tabs 62 to control an orientation of the base 52 with respect to the cut guide 12. In some embodiment, markings can be used to line-up the base 52 with the cut guide 12. The base 52 can also include a fixation slot 64 for receiving one or more wires inserted through the cut guide 12 and into the foot 48. In some embodiments, the fixation slot 64 provides for clearance of previously installed k-wires, pins, or other fixations devices.

The compression knob 54 and compression shaft 56 can be configured to position the compression head 58 with respect to the cut guide 12. For example, the base 52 can receive a portion of the compression shaft 56 (e.g., at an end distal from the through holes 60) and thereby position the compression head 58 relative to the foot 48. The compression knob 54 can be configured to move the compression head 58 relative to the cut guide 12, thereby compressing the foot 48 when the compression head 58 is fixed to the foot 48 at another location. The compression head 58 can include one or more fixation holes 66 for receiving wires fixed to the foot 48 and thereby accommodating a compression function. For example, the fixation holes 66 may receive pins or wires that extend into an adjacent metatarsal or other bones in the forefoot and/or midfoot as will be understood by one of ordinary skill in the art. The fixation hole(s) 66 can be any shape, number, angle, or size, depending on requirements of the procedure. The fixation holes 66 can be sized to accommodate a wire inserted into a sleeve to enhance bending strength while compressing. The fixation holes 66 can be configured to fix wires to the foot 48 in positions that enables compression, such as through pushing or pulling (depending on the fixation location). In some embodiments, a locking mechanism may be provided with a locking mechanism that locks the wires and/or pins within fixation holes 66. Such a locking mechanism may take a variety of configurations, including tapering within the holes 66 to provide a press-and/or interference-fit engagement between the pins or wires and the holes 66, one or more set screws for locking the pins or wires within the holes 66, and/or a detent, to list only a few implementations.

The compression knob 54 can be a turning knob or any style knob. The compression knob 54 can be retained with any retaining feature such as cross pins or a deformed end of threads. The compression shaft 56 can be partially threaded, fully threaded, or formed in another manner to enable relative motion. The compression shaft 56 an be D-shaped to control rotation or other shapes, such as double-D shape, hexagon shaped, etc.

Figure 6:
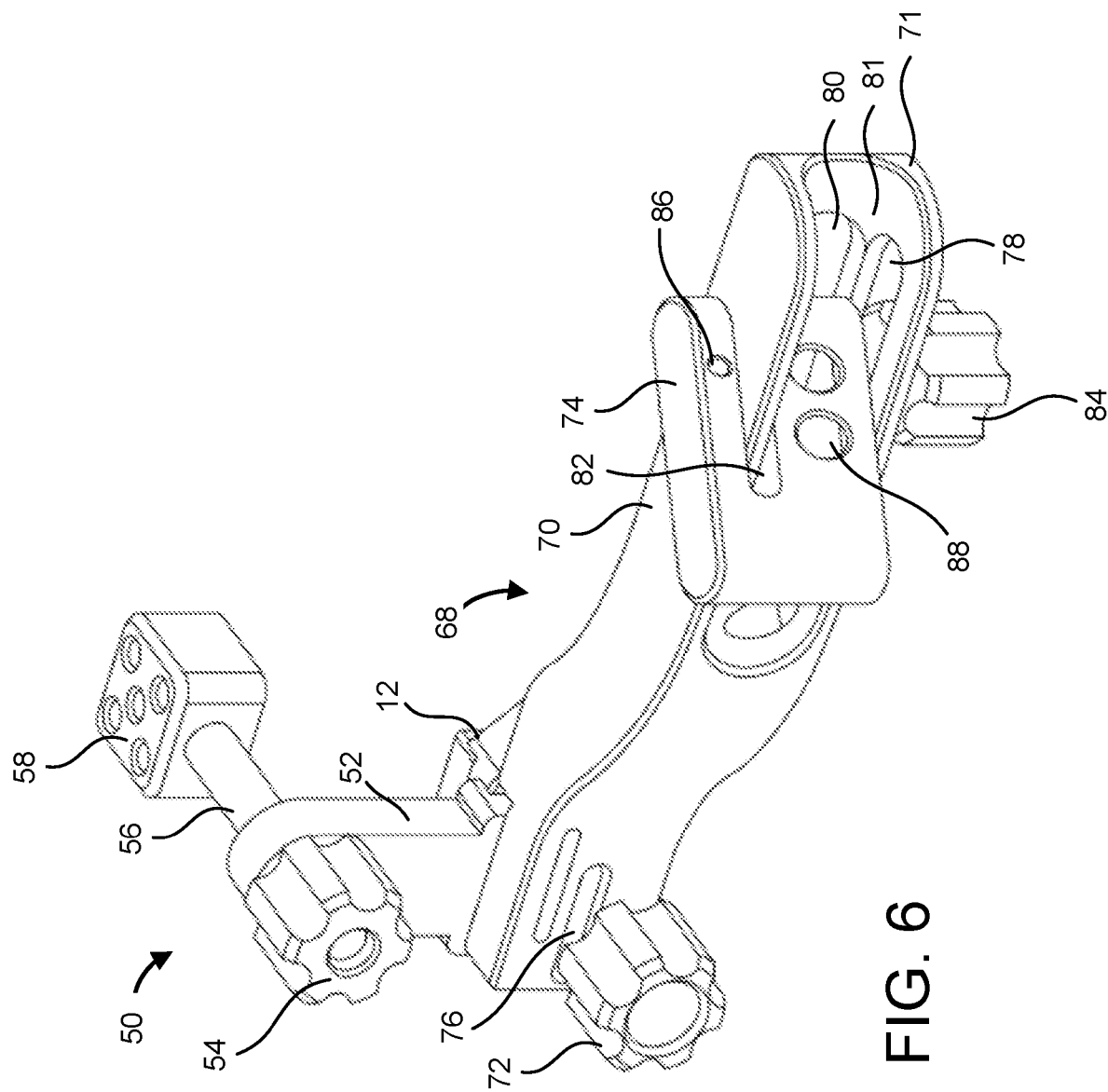
FIG. 6 is an isometric view of a slider mechanism attached to the cut guide of FIG. 1, according to disclosed embodiments.
Figure 7:
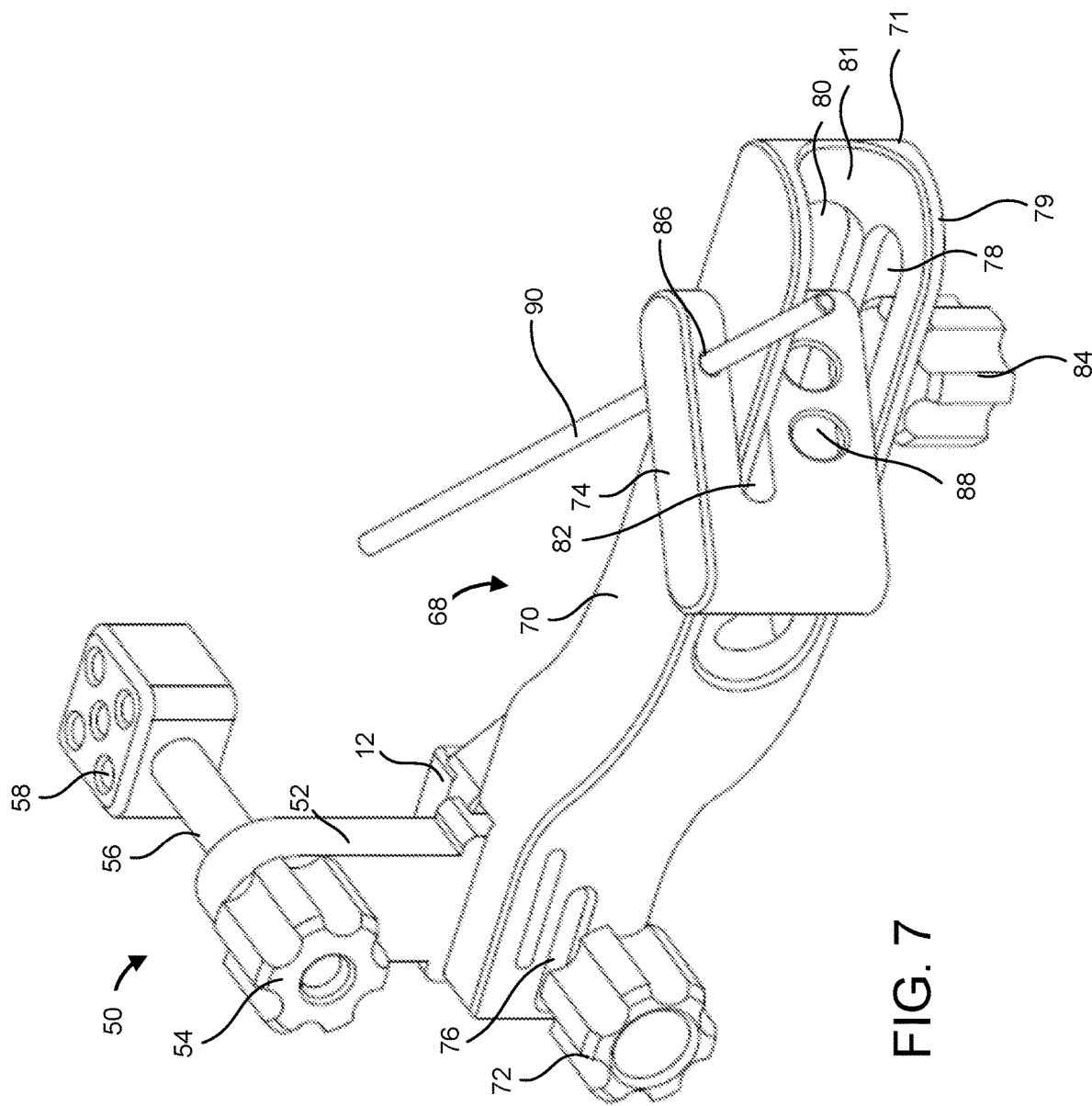
FIG. 7 is another isometric view of the system of FIG. 6, further include a wire positioned by the slider mechanism, according to disclosed embodiments.
Figure 8:
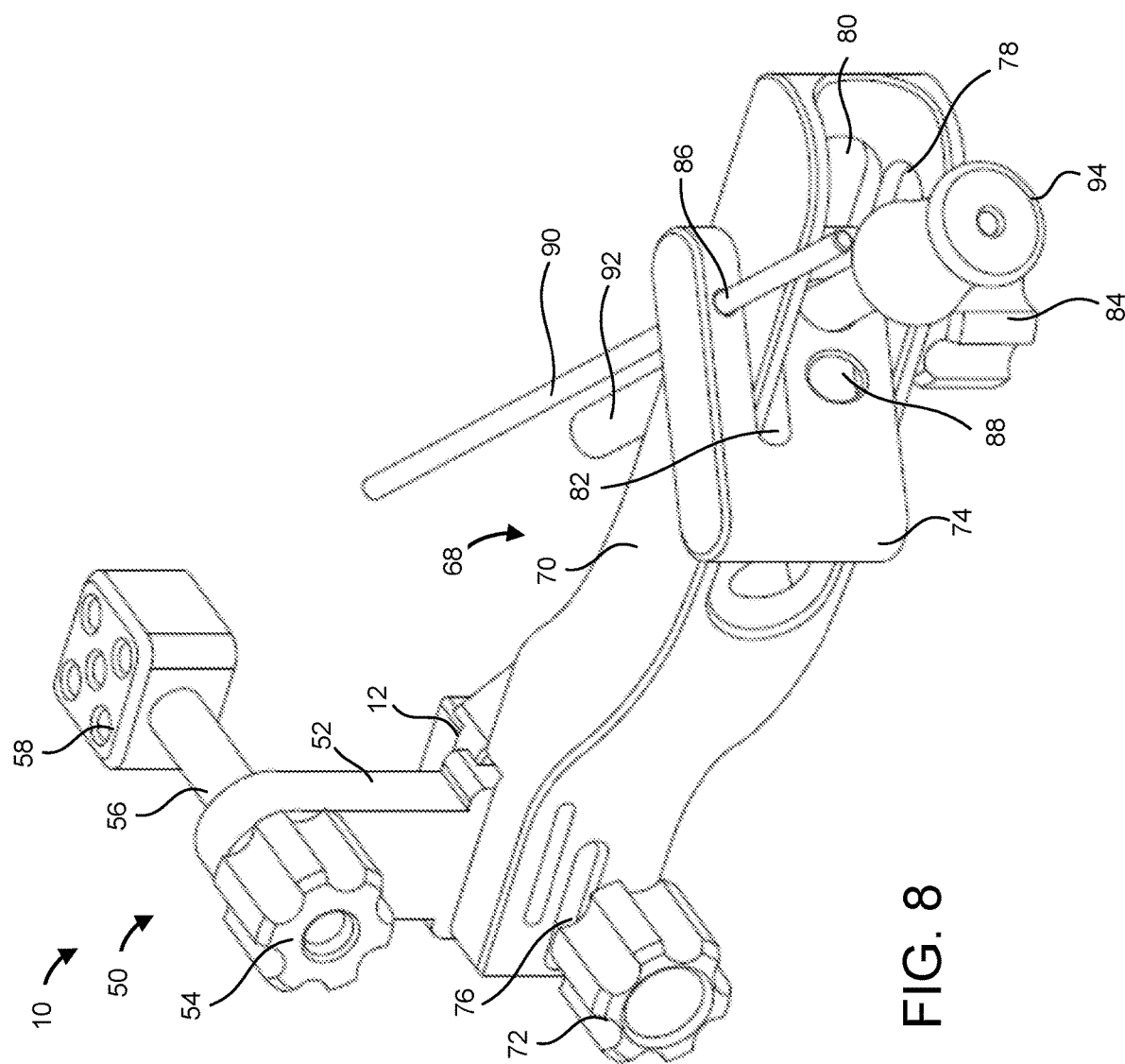
FIG. 8 is another isometric view of the system of FIG. 7, further including a sleeve positioned by the slider mechanism, according to disclosed embodiments.

FIGS. 6-8 illustrate an embodiment of a slider mechanism 68 attached to the cut guide 12. The slider mechanism 68, in some embodiments, is attached to the cut guide 12 through the base 52 of the compression device 50. The slider mechanism 68 can include an arm 70, a connector 72, and a slider 74. The arm 70 can be connected to the cut guide 12 and the compression device 50 by the connector 72. For example, the connector 72 can include a fastener configured to be inserted through an aperture in the arm 70, one of the through-holes 60 and into the attachment hole 46. The connector 72 can include a knob or other feature to tighten and loosen the fastener to accommodate attachment and removal. The arm 70 can include a fixation slot 76 for receiving one or more wires inserted through the cut guide 12 and into the foot 48. The fixation slot 76 can be a single slot or multiple slots and can be any shape. In some embodiments, arm 70 may include a clearance hole for receiving a pre-installed wire.

In some embodiments, the arm 70 includes slots 78, 80 formed in lower and side surfaces 79, 81 of a channel formed at an end 71 of the arm 70. The slider 74 can include a slot 82 configured to receive a portion of the arm 70 and thereby enable the slider 74 to slide and rotate with respect to the arm 70. The slot 78 can be formed to enable a locking mechanism 84 to tighten the slider 74 into a stationary position with respect to the arm 70. The slider 74 may include one or more holes 86, 88 for receiving additional components for use in the medical procedure. For example, the hole 86 can be configured for receiving a wire as shown in FIG. 7, such as a trajectory wire 90. In some embodiments, the trajectory wire 90 is able to slide in and out of the slider 74, although one of ordinary skill in the art will understand that a locking mechanism may be provided to lock trajectory wire 90 within hole 86. The trajectory wire 90 can be a measurement device for a screw, having notches and/or markings. The trajectory wire 90 can be a single piece design built into the slider 74.

In some embodiments, slider 74 may be provided with a locking mechanism to fix the location of slider 74 along channel 81. Such a locking mechanism may include one or more detents or protrusions and corresponding notches formed along a surface of channel 81 that provide a series of locations at which the slider 74 may be locked along channel 81. In some embodiments, slider 74 may include a set screw that is used to fix the position of the slider 74 along the channel 81 as will be understood by one of ordinary skill in the art.

The holes 86, 88 can be configured to receive a tool, such as a drill, for use in the medical procedure. In some embodiments, the hole 86 is positioned to be directed above the arm 70 and the hole 88 is positioned to be directed through the slot 80. Holes (e.g., holes 86, 88) in the slider 74 can be any size, shape or angle. The holes can be used for wire, depth gages, screws, drivers, sleeves, etc. In some embodiments a sleeve 92 and handle 94 are positioned with respect to one of the holes 88, as shown in FIG. 8.

The guiding system 10 includes the cut guide 12 having separate parts 14, 16 and fixation features for accommodating wires and attachment features for attaching the cut guide 12 to other components, such as the compression device 50 and slider mechanism 68. The components can be formed of any suitable materials and can be used in a medical procedure such as an operation on the foot 48 to address a hallux valgus deformity. One or more of the components, such as the compression device 50 and slider mechanism 68 can be made of radiolucent and/or radiopaque materials.

Figure 9:
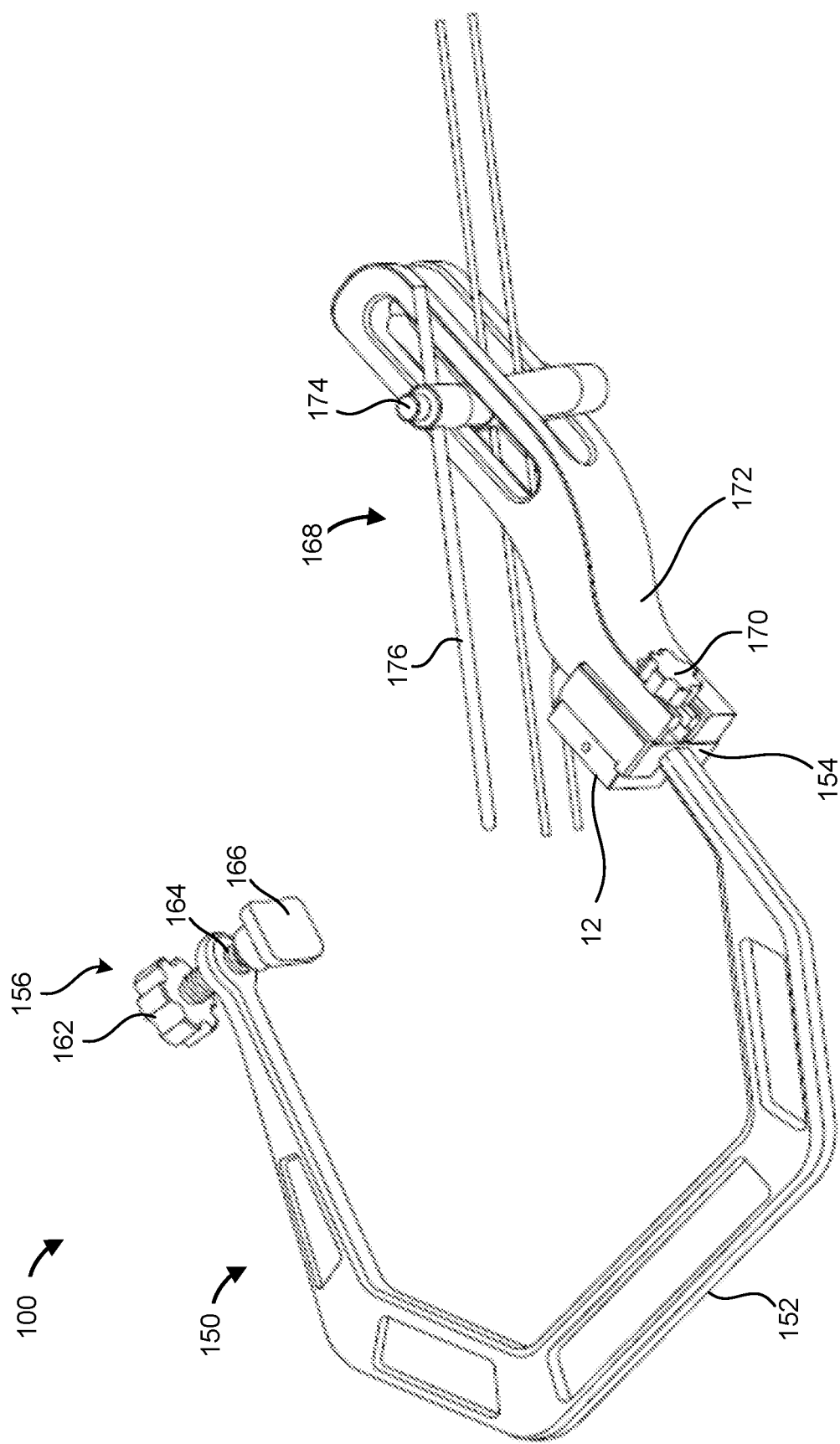
FIG. 9 is an isometric view of another embodiment of a compression device and slider mechanism that may be used in conjunction with the cut guide of FIG. 1, according to disclosed embodiments.
Figure 10:
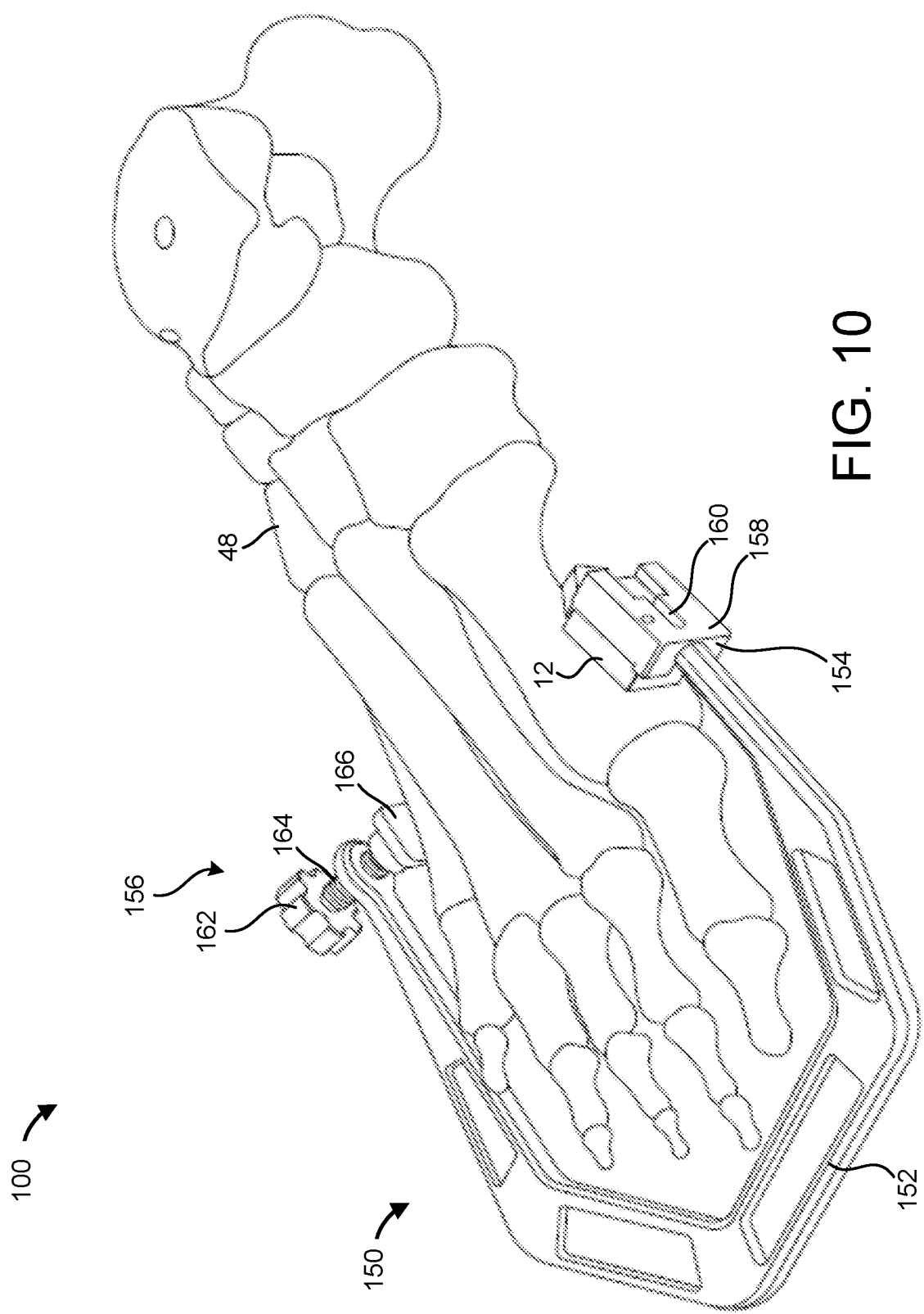
FIG. 10 is an isometric view of the compression device of FIG. 9 positioned in relation to a skeletal foot, according to disclosed embodiments.
Figure 11:
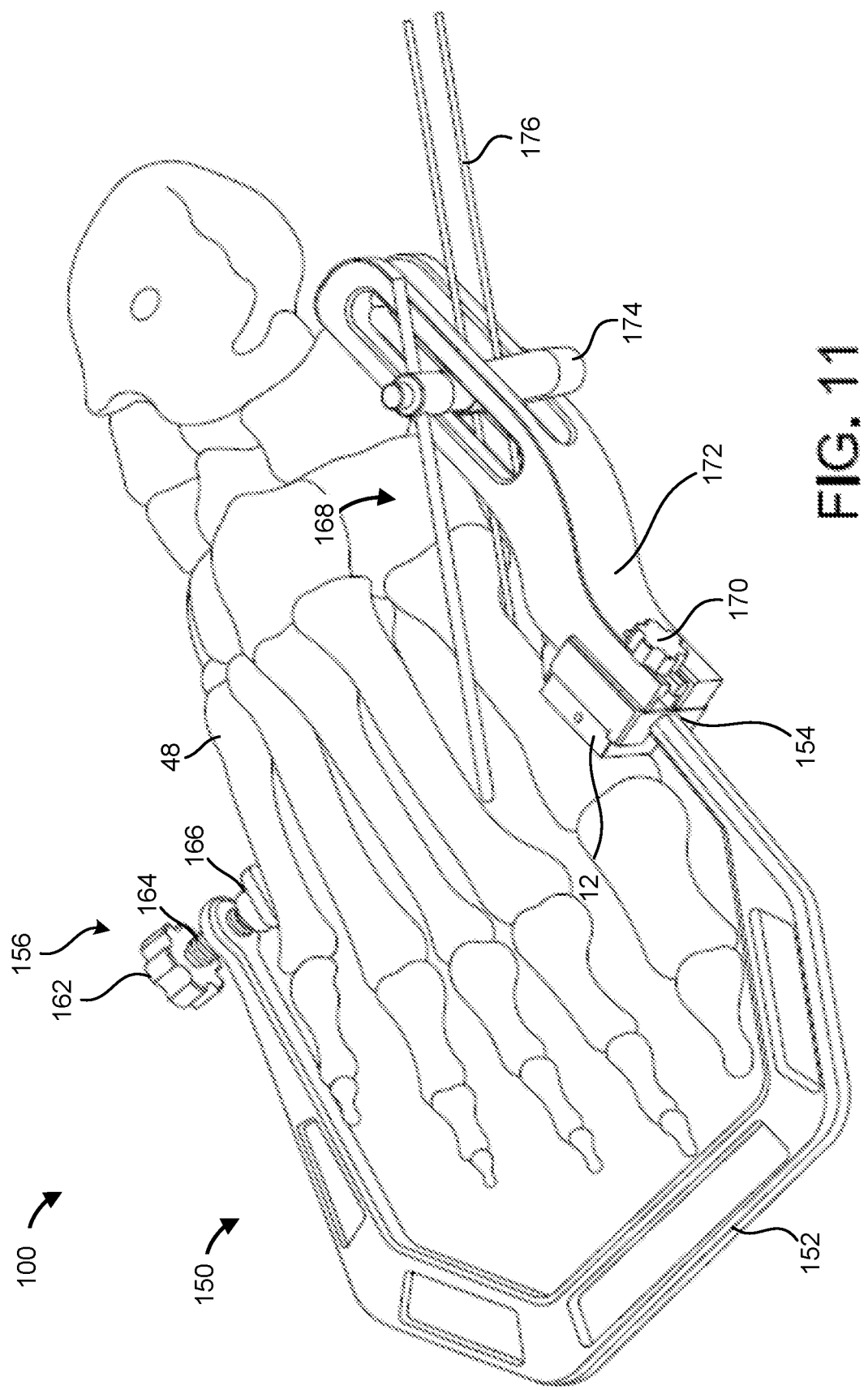
FIG. 11 is an isometric view of the compression device and slider mechanism of FIG. 9 positioned in relation to a skeletal foot, according to disclosed embodiments.

FIGS. 9-11 illustrate an another embodiment of a guiding device 100 including a compression device 150 and a slider mechanism 168 that can be used in combination with the cut guide 12 or a cut guide having similar fixation and attachment features. The compression device 150 can include a clamp arm 152, an attachment base 154, and a compressor 156. The clamp arm 152 can be attached to the cut guide 12 by the attachment base 154. The clamp arm 152 can include any shape, such as a generally arcuate shape that extends around the foot 48 to an opposite side of the foot 48 to position the compressor 156. For example, clamp arm 152 may extend across the top, bottom, and/or side of a foot as will be understood by one of ordinary skill in the art. The clamp arm 152 can include ergonomic features, grooves, textures, lightweight materials, etc. The attachment base 154 can include a through-hole 158 configured to be aligned with the attachment hole 46 of the cut guide 12. In some embodiments, the attachment base 154 can include or more alignment pins and the cut guide 12 can include corresponding alignment guide holes to receive the alignment pins and properly position the compression device 150 with respect to the cut guide 12 (e.g., with or without "attaching" the compression device 150 to the cut guide 12). The attachment base 154 can also include a fixation slot 160 for receiving one or more wires extending through the cut guide 12.

The compressor 156 can be positioned at a distal end of the clamp arm 152 to contact an opposite side of the foot 48 and thereby provide a compression force during a medical procedure. The compressor 156 can include, for example, a knob 162, a shaft 164, and a compression head 166. The compression head 166 can contact a portion of the foot 48 and move relative to the clamp arm 152 through rotation of the knob 162 and shaft 164.

The slider mechanism 168 can attach to the cut guide 12 and the compression device 150 by a locking screw 170 inserted through the through-hole 158 and into the attachment hole 46, thereby attaching the cut guide 12, the compression device 150, and the slider mechanism 168. The slider mechanism 168 can further include an arm 172 and a slider 174 configured to move relative to the arm 172. The slider 174 can accommodate wires 176 and/or other features in a manner similar to the slider 74.

The disclosed embodiments provide an all-in-one system for performing a medical procedure, such as a chevron resection together with additional fixation, compression, and/or guiding techniques for correcting a foot deformity or injury. The disclosed embodiments include a cut guide having both fixation features and attachment features to enable a simple and efficient interconnected process for completing the medical procedure.

Figure 12:
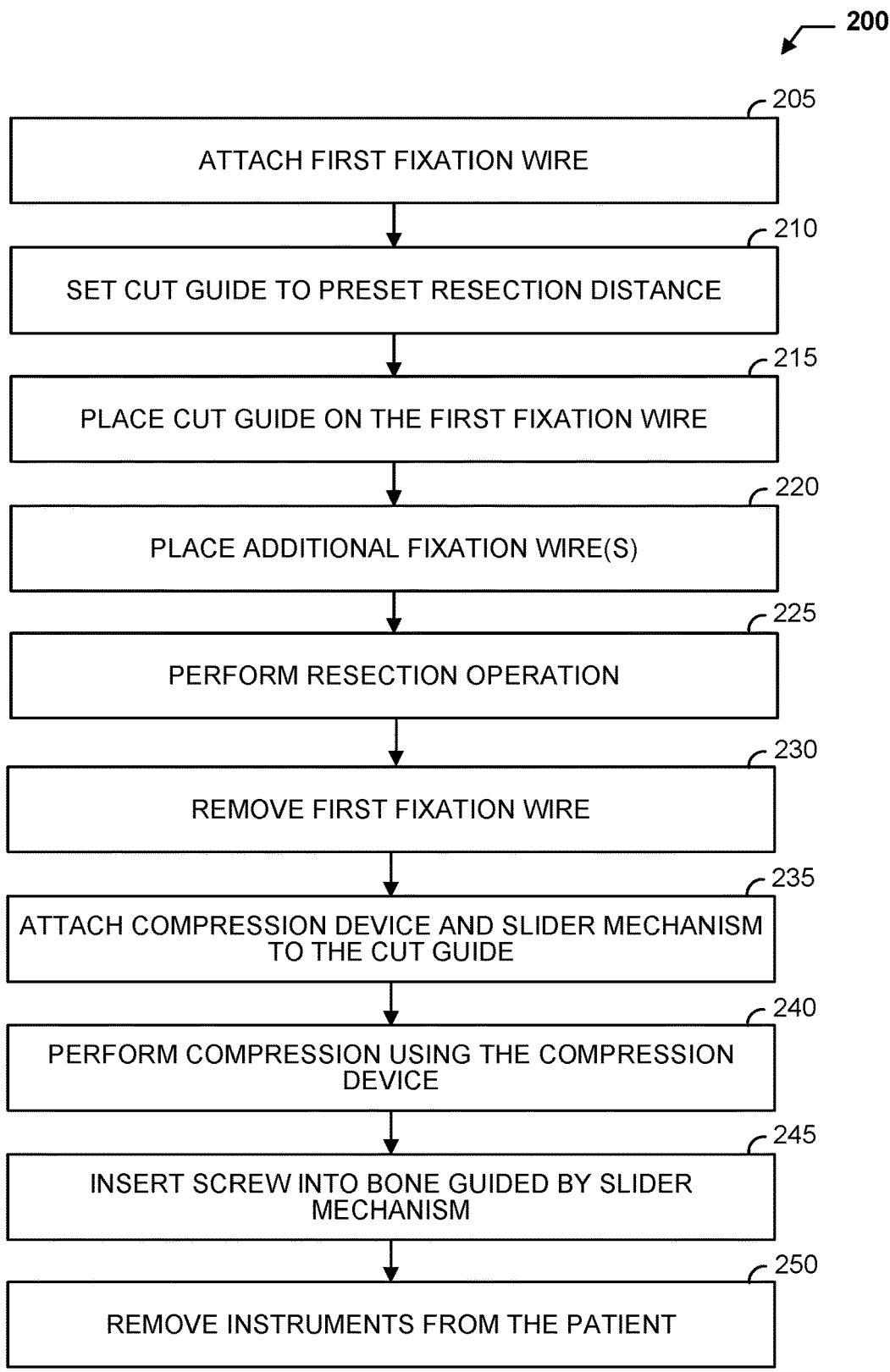
FIG. 12 is a flowchart of one example of a process for performing a medical procedure using a cut guide and other disclosed features, according to disclosed embodiments.

FIG. 12 is a flowchart of an exemplary process 200 for using the guiding system 10 in a medical procedure in accordance with some embodiments. The process 200 can include steps completed during a surgical procedure, including a minimally invasive surgery on a patient's foot.

At block 205, a first fixation wire is attached to a first metatarsal head. The wire can be attached using medical tools, steps, and preparation for attaching wire (e.g., k-wire) to bone, with care paid especially to dorsal-plantar alignment in the wire placement.

At block 210, the cut guide 12 is set to a preset resection distance through the sliding mechanism 34 and locking mechanism 36. For example, the cut guide 12 can be placed in the extended or collapsed configuration.

At block 215, the cut guide 12 is placed on the first fixation wire and slid until contact is made with the patient's foot. For example, the first fixation wire can be inserted through the first fixation hole 38 and the fixation clearance slot 42, and the cut guide 12 slid into place.

At block 220, at least one additional fixation wire can be placed, such as an oblique or straight wire. For example, a wire can be attached to the skeletal foot of the patient through the second fixation hole 40 and another fixation wire may be inserted into the fixation clearance slot 42. In another example, a fixation wire can be placed through the fixation hole 44. In some embodiments, the at least one additional fixation wire is placed after alignment of the cut guide 12 along an axis of a first metatarsal is determined.

At block 230, a chevron resection can be completed using the cut guide 12 and resection tools. For example, the first and second apertures 18, 20 and the first hole 26 can be used as guides for completing a chevron resection with the cut guide 12. In some embodiments, the first fixation wire placed in step 205 can be removed from the first metatarsal head and the cut guide 12 retracted once the resection has been completed.

At block 235, a compression device, such as compression device 50 or 150, and a slider mechanism, such as slider mechanism 68 or 168, can be attached to the cut guide by a locking screw. For example, a fastener can be inserted through aligned through-holes in the compression device 50, 150 and the slider mechanism 68, 168 and into the attachment hole 46 in the cut guide to attach the compression device and the slider mechanism in place.

At block 240, compression of the resected metatarsal head can be completed. For example, the compression knob 54 can be turned to compress the foot from another fixation point.

At block 245, one or more screws are inserted into the foot (during or after compression) using the slider mechanism as a guide. For example, the slider 74 can be moved to a desired position using the trajectory wire 90 as a template for the screw trajectory. After the trajectory is set, the slider can be locked into position. A drill sleeve and wire can then be inserted into the locked slider to measure depth for screw (e.g., using a depth gage). A drill can be used to create hole for screw in bone and the screw can thereafter be inserted with a driver. Holes in the slider can be used to align one or more of the wire, depth gage, sleeve, drill, driver, screw, etc. In some embodiments, additional screws may be inserted into a patient's foot. The additional screw(s) may be inserted parallel to the first screw, or the additional screw may be inserted such that it is non-parallel to the first screw.

At block 250, the instruments may be removed from the patient.

The disclosed embodiments provide a guiding system for performing medical operations, such as the process described above in relation to FIG. 12. It should be understood, however, that other operations are possible using the disclosed cut guide and the additional components described herein. According to disclosed embodiments, unlike other guiding systems, the cut guide includes attachment features for attaching additional mechanism to the patient's foot. This helps to reduce the number of required steps in comparison to other processes in which a cut guide can first be removed completely from the patient's foot before other components are attached. Further, the disclosed embodiments include fixation features, including a plurality of fixation options that can be utilized depending on need, and clearance features that help to adapt the cut guide for various implementations, including options for adjusting preset resection distances, multiple fixation holes, and slots for accommodating wires while allowing for the attachment of additional components.

In some embodiments, a cut guide includes a body having a first face and an opposed second face. The first face of the body defines first and second apertures, a first fixation hole, and an attachment hole. The first and second apertures are configured to guide a surgical tool, and the first fixation hole extends through the cut guide from the first face to the second face and is configured to receive a wire to position the cut guide against a bone. The attachment hole is configured to attach the cut guide to another component.

In some embodiments, the body includes a first part and a second part.

In some embodiments, a sliding mechanism is configured to enable relative movement of the first part and the second part.

In some embodiments, the first part defines a retaining slot and the second part includes a retaining pin for limiting the relative movement of the first part and the second part.

In some embodiments, the first part includes a retaining pin and the second part defines a retaining slot. The retaining pin is sized and configured to be received within the retaining slot, and the combination of the retaining pin and the retaining slot limit the relative movement of the first part and the second part.

In some embodiments, the first part comprises the first aperture, the second aperture, the first fixation hole, and the attachment hole.

In some embodiments, the second part comprises a fixation clearance slot aligned with the first fixation hole of the first part.

In some embodiments, the second part comprises a contacting surface configured to contact a patient.

In some embodiments, the second part defines a second fixation hole.

In some embodiments, the first part and the second part are relatively movable between an extended position and a collapsed position.

In some embodiments, a locking mechanism biases the first part and the second part into one or more of the extended position and the collapsed position.

In some embodiments, the first attachment hole is threaded.

In some embodiments, the first and second apertures extend through the cut guide from the first face to the second face.

In some embodiments, the first aperture is a first elongate slot defining a first longitudinal axis, the second aperture is a second elongate slot defining a second longitudinal axis, and the first longitudinal axis is oriented at an angle with respect to the second longitudinal axis.

In some embodiments, the angle is an oblique angle. In some embodiments, the angle is a right angle.

In some embodiments, a system includes a cut guide, a compression device, and a a first connector. The cut guide has a body including a first face and an opposed second face. The first face of the body defines first and second apertures, a first fixation hole, and an attachment hole. The first and second apertures are configured to guide a surgical tool. The first fixation hole extends through the cut guide from the first face to the second face and is configured to receive a wire to position the cut guide against a bone. The compression device has a base and a compression head, which is movable relative to the base. The first connector is sized and configured to couple to the compression device to the cut guide via the attachment hole.

In some embodiments, a slider mechanism is provided that has an arm and a slider supported by the arm. The arm defines a second attachment hole sized and configure to receive the first connector therethrough to couple together the cut guide, slider mechanism, and compression device.

In some embodiments, the compression device includes a compression knob and a compression shaft connected to the compression head. The compression knob is configured to move the compression head relative to the base in response to being rotated.

In some embodiments, the compression head includes one or more fixation holes for receiving a wire to fix the compression head to bone.

In some embodiments, the one or more fixation holes are disposed at an angle with respect to the first fixation hole defined by the cut guide.

In some embodiments, the one or more fixation holes are arranged perpendicular with respect to the first fixation hole defined by the cut guide.

In some embodiments, the base defines a fixation clearance slot configured to be aligned with the first fixation hole to receive the wire extending through the first fixation hole.

In some embodiments, the base includes an alignment feature for aligning the compression device with the cut guide.

In some embodiments, the slider defines a slot configured to receive a portion of the arm such that the slider is slidable and rotatable with respect to the arm.

In some embodiments, a locking mechanism is configured to lock the slider in a selected position relative to the arm.

In some embodiments, the slider includes one or more holes for inserting a wire, sleeve, or tool therethrough.

In some embodiments, a method includes coupling a first wire to a first bone of an appendage of a patient; coupling a cutting guide to the first wire; inserting a second wire into a first fixation hole defined by the cutting guide and into the first bone; resecting the first bone using a surgical tool and the cutting guide; attaching a compression device to the cutting guide; and compressing the appendage of the patient using the compression device.

In some embodiments, the bone is a first metatarsal.

In some embodiments, coupling the cutting guide to the first wire includes aligning a second fixation hole defined by the cutting guide with an end of the first wire and sliding the cutting guide over the first wire such that the first wire is received within the second fixation hole.

In some embodiments, a method includes attaching a slider mechanism to the cutting guide.

In some embodiments, a method includes inserting at least one screw into a bone of the patient's foot using the slider mechanism as a guide and removing the first wire, the second wire, the cutting guide, the compression device, and the slider mechanism from the patient's foot.

In some embodiments, a method includes inserting at least one fixation device through a hole defined by the compression device and into the appendage.

In some embodiments, compressing the appendage of the patient includes rotating a compression knob of the compression device.

Although the invention has been described in terms of exemplary embodiments, it is not limited thereto. Rather, the appended claims should be construed broadly, to include other variants and embodiments of the invention, which can be made by those skilled in the art without departing from the scope and range of equivalents of the invention.

What is claimed is:

1. A cut guide, comprising:
    a body comprising a first face and an opposed second face, the first face of the body defining:
        a first aperture and a second aperture, the first and second apertures configured to guide a surgical tool;
        a first fixation hole extending through the cut guide from the first face to the second face, the first fixation hole configured to receive a wire to position the cut guide against a bone;
        a first attachment hole configured to attach the cut guide to another component; and
    a slider mechanism having an arm with a slider supported by the arm, the arm defining a second attachment hole sized and configure to receive a first connector to couple together a cut guide, the slider mechanism, and a compression device.

2. The cut guide of claim 1, wherein the body comprises a first part and a second part.

3. The cut guide of claim 2 wherein the sliding mechanism is configured to enable relative movement of the first part and the second part.

4. The cut guide of claim 3, further comprising a retaining slot and a retaining pin for limiting the relative movement of the first part and the second part.

5. The cut guide of claim 2, wherein the first part comprises the first aperture, the second aperture, the first fixation hole, and the attachment hole.

6. The cut guide of claim 5, wherein the second part comprises a fixation clearance slot aligned with the first fixation hole of the first part.

7. The cut guide of claim 5, wherein the second part comprises a contacting surface configured to contact a patient.

8. The cut guide of claim 5, wherein the second part comprises a second fixation hole.

9. The cut guide of claim 2, wherein the first part and the second part are relatively movable between an extended position and a collapsed position.

10. The cut guide of claim 9, further comprising a locking mechanism for biasing the first part and the second part into one or more of the extended position and the collapsed position.

11. The cut guide of claim 1, wherein the first attachment hole is threaded.

12. The cut guide of claim 1, wherein the first and second apertures extend through the cut guide from the first face to the second face.

13. The cut guide of claim 12, wherein
    the first aperture is a first elongate slot defining a first longitudinal axis,
    the second aperture is a second elongate slot defining a second longitudinal axis, and
    the first longitudinal axis is oriented at an angle with respect to the second longitudinal axis.

14. The cut guide of claim 13, wherein the angle is an oblique angle.

15. The cut guide of claim 13, wherein the angle is a right angle.

16. A system, comprising:
    a cut guide, comprising a body comprising a first face and an opposed second face, the first face of the body defining:
        a first aperture and a second aperture, the first and second apertures are configured to guide a surgical tool;
        a first fixation hole extending through the cut guide from the first face to the second face, the first fixation hole configured to receive a wire to position the cut guide against a bone; and
        an attachment hole;
    a compression device comprising a base and a compression head, the compression head movable relative to the base;
    a first connector sized and configured to couple to the compression device to the cut guide via the attachment hole; and
    a slider mechanism having an arm and a slider supported by the arm, the arm defining a second attachment hole sized and configure to receive the first connector therethrough to couple together the cut guide, slider mechanism, and compression device.

17. The system of claim 16, wherein the compression device includes a compression knob and a compression shaft connected to the compression head, the compression knob configured to move the compression head relative to the base in response to being rotated.

18. The system of claim 17, wherein the compression head comprises one or more fixation holes for receiving a wire to fix the compression head to bone.

19. The system of claim 18, wherein the one or more fixation holes are disposed at an angle with respect to the first fixation hole defined by the cut guide.

20. The system of claim 18, wherein the one or more fixation holes are arranged perpendicular with respect to the first fixation hole defined by the cut guide.

21. The system of claim 16, wherein the base defines a fixation clearance slot configured to be aligned with the first fixation hole to receive the wire extending through the first fixation hole.

22. The system of claim 16, wherein the base comprises an alignment feature for aligning the compression device with the cut guide.

23. The system of claim 16, wherein the slider defines a slot configured to receive a portion of the arm such that the slider is slidable and rotatable with respect to the arm.

24. The system of claim 23, further comprising a locking mechanism configured to lock the slider in a selected position relative to the arm.

25. The system of claim 24, wherein the slider comprises one or more holes for inserting a wire, sleeve, or tool therethrough.

\* \* \* \* \*